United States Patent
Lindner et al.

(10) Patent No.: US 9,518,134 B2
(45) Date of Patent: *Dec. 13, 2016

(54) WATER-ABSORBENT SURFACE-MODIFIED-CLAY LINKED POLYMERS

(75) Inventors: Torsten Lindner, Schwalbach (DE); Axel Meyer, Schwalbach (DE); Michael Moeller, Schwalbach (DE); Josef Breu, Bayreuth (DE); Manuela Stirner, Bayreuth (DE)

(73) Assignee: The Procter & Gamble Company, Cincinnati, OH (US)

( * ) Notice: Subject to any disclaimer, the term of this patent is extended or adjusted under 35 U.S.C. 154(b) by 17 days.

This patent is subject to a terminal disclaimer.

(21) Appl. No.: 13/326,376

(22) Filed: Dec. 15, 2011

(65) Prior Publication Data

US 2012/0157623 A1    Jun. 21, 2012

(30) Foreign Application Priority Data

Dec. 15, 2010    (EP) .................................... 10195087

(51) Int. Cl.
| | |
|---|---|
| *C08F 2/44* | (2006.01) |
| *A61L 15/60* | (2006.01) |
| *C09C 1/42* | (2006.01) |
| *A61L 15/18* | (2006.01) |

(52) U.S. Cl.
CPC .................. *C08F 2/44* (2013.01); *A61L 15/60* (2013.01); *C09C 1/42* (2013.01); *A61L 15/18* (2013.01); *C01P 2004/20* (2013.01); *C01P 2004/22* (2013.01); *C01P 2004/54* (2013.01); *C08J 2300/14* (2013.01)

(58) Field of Classification Search
CPC ........ A61L 15/18; A61L 15/60; C08J 2300/14
USPC ................... 524/444, 445, 789, 790
See application file for complete search history.

(56) References Cited

U.S. PATENT DOCUMENTS

| | | | | |
|---|---|---|---|---|
| 3,068,185 | A * | 12/1962 | Stamberger ................... | 523/209 |
| 4,412,018 | A * | 10/1983 | Finlayson et al. ............ | 523/508 |
| 4,885,161 | A * | 12/1989 | Cornell ............... | A61L 26/0052 |
| | | | | 424/447 |
| 5,498,662 | A * | 3/1996 | Tanaka ....................... | C08J 5/18 |
| | | | | 524/27 |
| 6,646,086 | B2 | 11/2003 | Slone | |
| 2003/0105208 | A1* | 6/2003 | Twardowska et al. ........ | 524/445 |
| 2003/0176537 | A1* | 9/2003 | Chaiko ......................... | 523/200 |
| 2004/0071622 | A1* | 4/2004 | Lin et al. ...................... | 423/335 |
| 2006/0199889 | A1* | 9/2006 | Hunter et al. ................. | 524/445 |
| 2006/0199890 | A1* | 9/2006 | Fasulo et al. ................. | 524/445 |
| 2007/0199481 | A1* | 8/2007 | Roelofs ......................... | 106/487 |
| 2007/0225422 | A1* | 9/2007 | Sakamoto ................ | C08F 2/44 |
| | | | | 524/458 |
| 2008/0146719 | A1* | 6/2008 | Yang et al. .................... | 524/445 |
| 2009/0318598 | A1* | 12/2009 | Perez et al. ................... | 524/261 |
| 2012/0157622 | A1* | 6/2012 | Lindner et al. ............... | 524/790 |
| 2012/0157623 | A1* | 6/2012 | Lindner et al. ............... | 524/790 |
| 2012/0310196 | A1* | 12/2012 | Haeberle et al. ............. | 604/372 |
| 2013/0043384 | A1* | 2/2013 | Matsumoto ........... | C08F 220/06 |
| | | | | 250/282 |
| 2015/0307667 | A1* | 10/2015 | Wada ....................... | C08J 3/245 |
| | | | | 252/194 |

FOREIGN PATENT DOCUMENTS

| | | | |
|---|---|---|---|
| JP | 05-202903 B2 | | 6/2013 |
| WO | WO 2009/041870 | * | 2/2009 |

OTHER PUBLICATIONS

International Search Report, PCT/US2011/064889, mailed Feb. 20, 2012, 8 pages.
Lee, W-F, "Preparation of Reactive Mineral Powders Used for Poly(sodium acrylate) Composite Superabsorbents", Journal of Applied Polymer Science, J. Wiley & Sons, Inc., vol. 97, No. 3, Aug. 5, 2005, pp. 855-861, XP02604080.

* cited by examiner

Primary Examiner — Michael A Salvitti
(74) Attorney, Agent, or Firm — Andrew J. Mueller; Andrew A Paul; Richard L. Alexander

(57) ABSTRACT

An aqueous acidic polymerization liquid comprising polymerizable monomers or oligomers with carboxylate and/or carboxylic acid moiety or moieties, and basal surface modified clay that is homogenously dispersable in said liquid is provided, and also methods for making such liquids, and also surface-modified-clay linked water-absorbing polymers made with said liquids and methods, and disposable absorbent articles comprising such surface-modified-clay linked water-absorbing polycarboxylate/polycarboxylic acid polymers.

25 Claims, No Drawings

WATER-ABSORBENT SURFACE-MODIFIED-CLAY LINKED POLYMERS

FIELD OF THE INVENTION

An aqueous acidic polymerization liquid comprising polymerisable monomers and surface-modified-clay that is homogenously dispersable in said liquid, and to methods for making such liquids, and to water-absorbing surface-modified-clay linked (SMC) polymers made with said liquids or made by said methods herein, and absorbent articles containing these water-absorbing SMC polymers.

BACKGROUND OF THE INVENTION

An important component of disposable absorbent articles such as diapers is an absorbent core structure comprising water-absorbing polymers, e.g. hydrogel-forming and/or water-swellable polymers, also referred to as absorbent gelling material, AGM, or super-absorbent polymers, or SAP's. This polymer material ensures that large amounts of bodily fluids, e.g. urine, can be absorbed by the article during its use and locked away, thus providing low rewet and good skin dryness.

Especially useful water-absorbing polymers or SAP's are often made by initially polymerizing unsaturated carboxylic acids or derivatives thereof, such as acrylic acid, alkali metal (e.g., sodium and/or potassium) or ammonium salts of acrylic acid, alkyl acrylates, and the like in the presence of cross-linking compounds, such as (relatively small amounts of) di- or poly-functional monomers such as N,N'-methylenebisacrylamide, trimethylolpropane triacrylate, ethylene glycol di(meth)acrylate, or triallylamine. The di- or poly-functional monomer materials serve to cross-link the polymer chains thereby rendering them water-insoluble, yet water-swellable. These cross-linked absorbent polymers contain a multiplicity of carboxylate groups attached to the polymer backbone. It is generally believed, that the neutralized carboxylate groups generate an osmotic driving force for the absorption of body fluids by the cross-linked polymer network.

Such reactions are typically done with aqueous solutions of the monomers and crosslinking agents, because a solution polymerization has been found to be most efficient and effective to provide (uniformity in) polymers, and water is typically the preferred reaction solvent (e.g. for safety and cost reasons). Thus, typically electrolyte monomers, such as (partially) neutralized unsaturated carboxylic acids (i.e. unsaturated carboxylate salts), and crosslinking agents are used in the form of an aqueous solution (the resulting water-absorbing polymers being cross-linked polyelectrolyte (e.g. polycarboxylate) polymers).

In recent years, some absorbent polymers that are linked by nano-sized clay particles have been proposed. Unlike some superabsorbent material whereby clay is added after polymerization, it has been found to be important that the clay is added in nano-size prior to polymerization, to ensure the clay form strong links between the polymers. This is for example described in "Nanocomposite Polymer Gels"; Schexnailder/Schmidt; *Coloid Polym Sci* (2009) 287: 1-11. Some of said clay linked polymers form elastic or stretchable hydrogels upon swelling. For example, water-containing hydrogel shaped or molded articles, comprising certain specific isopropyl polyamides linked by certain clay particles are described in *Macromolecules* 2002, 35, 10162-10171 (Kazutoshi Haraguchi et all); these elastic, shaped hydrogels are intended for medical purposes where they can be used in applications where they can de-water quickly, and thus shrink, upon demand, e.g. driven by temperature changes. WO 2009/041870 and WO 2009/041903 describe the desire to make clay linked polyacrylates, but that polyacrylates cannot be linked by nano-size clay particles successfully, because the clay aggregates in the presence of acrylate or acrylic acid. They teach thereto fibers, foams and films (that may be made in particles) of clay linked hydrogels, made by mixing nano-size clay particles and acrylic esters in a liquid to form clay linked polyacrylic esters, that may be shaped in foams, fibers, films etc. These polyacrylic ester shapes are then hydrolyzed using conventional hydrolysis techniques in order to obtain polyacrylate shapes. However, the hydrolyses of complete foams, fibers or gels, or even batches of finished particles of polyacrylic esters is a very slow and energy-demanding process, because the penetration of the hydrolysis solution is driven by diffusion only which is a generally slow process. Furthermore, it is difficult to achieve a very homogeneous hydrolysis throughout the entire polymer shapes, even if such shapes are made into particles, i.e. some parts of the polymer may be hydrolyzed earlier and to a larger extent than others. Furthermore, by-products from the hydrolysis (such as methanol or ethanol) would need to be removed from the product, and the level of these by-products would need to be brought to very low levels (toxicity, odour).

Thus, the proposed clay linked polyester shapes, and the hydrolysis thereof are not suitable for commercial scale production of (e.g. particulate) clay linked polyacrylates (particles).

The present invention however provides polymerization reaction liquids that allow homogeneous clay platelet dispersion in the presence of the polymerizable carboxylate/carboxylic acid monomers or oligomers, i.e. in an acid liquid, without or with very little aggregation of clay. The dispersed clay platelets can thus link the polymers during polymerization in a very uniform manner. Furthermore, the process is such that no subsequent ester-hydrolysis is required. The thus obtained clay linked polycarboxylate/polycarboxylic acid polymers can be suitably incorporated in absorbent articles.

SUMMARY OF THE INVENTION

Provided are water-absorbing basal surface-modified-clay linked polycarboxylic acid and/or polycarboxylate polymers, obtainable by a polymerization reaction comprising the steps of:

a) obtaining an aqueous polymerization reaction liquid, comprising i) homogeneously dispersed therein, clay platelets with opposing basal platelet surfaces and platelet edges; and ii) dissolved or homogeneously dispersed therein, a polymerizable monomers comprising a carboxylic acid group and/or carboxylate group, and/or polymerizable oligomers of one or more of said monomers;

whereby said aqueous liquid has a pH of 6 or less, and whereby said basal surface(s) of said clay platelets are modified with a surface modification compound(s);

b) initiating the polymerization of said monomers and/or oligomers in said liquid of step a).

Also provided is a method for making water-absorbing surface-modified-clay linked polycarboxylic acid and/or polycarboxylate polymers, comprising the steps of:

a) obtaining an aqueous polymerization reaction liquid comprising i) homogeneously dispersed therein, clay platelets with opposing basal platelet surfaces and platelet edges;

and ii) dissolved or homogeneously dispersed therein, a polymerizable monomers comprising a carboxylic acid group and/or carboxylate group, and/or polymerizable oligomers of one or more of said monomers;

whereby said aqueous liquid has a pH of 6 or less; and whereby said basal surface(s) of said clay platelets are modified with a surface modification compound(s);

b) obtaining an polymerization initiator system;

c) combining said liquid of a) with said polymerization initiator system of b) and polymerizing said monomers and/or oligomers.

Said water-absorbing surface-modified-clay linked polymers are herein referred to as water-absorbing SMC polymers. The SMC polymers may be i) SMCpolycarboxylic acid polymers, that are not neutralized, or ii) SMC polycarboxyalte polymers, that are fully neutralized, or iii) SMC polymers that have carboxylate and carboxylic acid groups (e.g. at any of the mol % levels stated herein). Any of these EMC polymers i), ii) or ii) or mixtures thereof is herein referred to as EMC polycarboxylate and/or polycarboxlic acid polymers.

Also provided is a method for making such polymers, as described herein below.

It has been found that by modifying the clay platelet surfaces as set out herein, the clay platelets can be better dispersed in the acidic polymerization liquid with carboxylic acid monomers and/or carboxylate monomers, or oligomers thereof, required to form the polycarboxylic acid/polycarboxylate polymers. The basal surface modification compounds may rendering the platelet surfaces for example neutral at (e.g. at least at) the liquid's pH, e.g. at said pH of 6 or less; or optionally at a range of pH levels from pH 6 or less and below, e.g. at a range of pH levels from 3 to 6, or from 3 to 5.5, or to 5. Unlike unmodified clay platelets that have in acidic water positive edges that are attracted to the negative basal surfaces of the platelets, which cause aggregation of said clay platelets, the surface-modified clay platelets have a very reduced tendency to form aggregates in acidic water. Thereby, aqueous acidic liquids comprising homogeneously dispersed edge-modified clay platelets can be obtained. In preferred embodiment herein, said resulting aqueous polymerization reaction liquid is, at least prior to commencement of the polymerization reaction, a microscopic homogeneous dispersion.

It is believed that such water-absorbing SMC polymers, whereby said polymers are linked by said surface-modified-clay platelets, obtained via a method/liquid whereby said surface-modified clay is substantially homogeneously dispersed, have a narrower distribution of the length of the polymer chain segments between two linking points (e.g. two clay platelets). It is thus believed that they are hence able to (substantially) all move and expand to a similar extend when the water-absorbing SMC polymers swell due to fluid-absorption. It is believed that mechanistically, the polymers connected to the same modified-clay platelet sustain a force (stretching or pressure) cooperatively; this then increases the elongation to break compared to traditional linked polymer networks, whereby the linking is only achieved by organic crosslinking groups. The SMC polymers may have an increased resistance to shear stress/strain. This reduces deformation and hence gel blocking. Furthermore, it is believed that due to the hydrophilic nature of the clay platelets, the resulting SMC polymers can have an advantage in the absorption speed.

Said surface modification compound(s) may have a cationic moiety that can bind to a clay platelet's basal plate. In some embodiments, said surface modification compound has one or more alkylated nitrogen moieties and/or alkoxylated nitrogen moieties. In order to render the surface-modified clay more hydrophilic, said surface modification compound(s) may also having an anionic moiety or one or more hydroxyl groups. In some preferred embodiments herein the surface modification compound has one or more moieties that can ionically or covalently bind to the monomers, oligomers, or the polymers formed thereof; in some embodiments, said surface modification compound comprises a unsaturated moiety (such as a C=C group) that can be covalently bonded to said polymerizable monomer or polymerizable oligomer or said polymer, and/or said surface modification compound comprises a moiety that can be covalently or ionically bonded to said carboxy moiety of said monomer, oligomer or polymer (such as a hydroxyl group, such as from a oligo-alkyleneoxide, e.g. oligo-ethyleneoxide).

In some embodiments, said surface modification compound(s) is (are) a compound that sterically hinders said platelet surfaces, said compound having for example a length of at least 10 angstrom (A), preferably said compound having at least one moiety comprising a carbon chain of at least 6 carbon atoms.

In general, water-absorbing polyelectrolyte polymers provide the required osmotic pressure that drives the required absorption and retention of fluids like urine. Thus, in some embodiments here, in order to further increase the capacity of the water-absorbing SMC polymers herein, the polymers or part thereof may be polyelectrolytes, e.g. anionic polymers, made from negatively charged monomers. The polymerizable monomers or oligomers may be partially or completely neutralized, said all or part of said monomers or oligomers comprising thus at least one carboxylate group with a cationic counter ion, e.g. carboxylate salt monomers; e.g. at least 20 mol % (on the basis of all oligomers or monomers in the solution or dispersion, or in the polymer) of the monomers or oligomers are neutralized, e.g. at least 20 mol % has a carboxylate-containing monomers or oligomers, (e.g. monomers, such as acrylate), with a cationic counter ion, (e.g. sodium). Thus the resulting polymer may also be partially or completely neutralized, having for example at least 20 mol % of polymerized monomers or oligomers with a carboxylate group(s). In some embodiments, this mol percentage may be at least 40 mol %, or at least 60 mol %.

In some embodiments herein the addition of a dispersion aid may be useful, to be added to the polymerization reaction liquid, and/or prior to that, to the monomer or oligomer solution or dispersion, and/or to the clay dispersion, or to the edge-modified clay dispersion. This may in particular be useful when the monomer solution or oligomer solution/dispersion is partially or completely neutralized, e.g. comprising the carboxylate salt form, as described above and hereinafter. Useful dispersion aids include for example saccharides and oligo- or poly-saccharides, including for example carboxymethyl cellulose (CMC).

In some embodiments herein, the pH of the liquid may be from 3 to 5.5 or to 5.

In some embodiments herein, the clay edges may additionally be modified, as described herein, to further improve the homogeneous dispersion of the clay platelets, and hence to more homogeneously modified clay linked polymers, as described herein.

In another aspect of the invention, an aqueous polymerization reaction liquid is provided, which comprises i) homogeneously dispersed therein, clay platelets with opposing basal platelet surfaces and modified platelet edges; and ii) dissolved or homogeneously dispersed therein, acrylic acid/acrylate monomers, and/or polymerizable oligomers of said monomers, whereby said aqueous liquid has a pH of 6 or less and whereby said platelet edges are modified; whereby for example at least 20 mol % of said monomers and/or polymerizable oligomers is in the salt form.

Further embodiment of the invention herein relate to absorbent articles, such as feminine hygiene articles and diapers, comprising the SMC polymers herein.

In some embodiments herein, the aqueous polymerization liquid or method herein does not include any organic cross-linker compounds and the SMC polymers are free of organic crosslinking compounds that internally crosslink the polymers.

In some embodiments herein, the aqueous polymerization liquid or method herein include an organic cross-linker compound and the SMC polymers comprises organic cross-linking compounds that internally crosslink the polymers.

In the polymerization liquid and/or in the SMC polymers the weight ratio of: (clay) to (monomer and/or oligomer) may for example be up to 1:10, e.g. from 1:1000 or from 1:500, or from 1:200 to 1:10, or to 1:7 or to 1:5.

DETAILED DESCRIPTION OF THE INVENTION

Clay and Clay Platelets

The present invention requires the use of clay that can be dispersed as platelets in an acidic aqueous liquid. Clay platelets have opposing basal platelet surfaces, herein also referred to as "surfaces", and platelet edge surfaces, herein referred to as "edges" (since they are about 2D), and said basal surface of the platelet are for the purpose of the invention modified, as described herein. The surface modified clay platelets in the polymerization liquid are preferably homogeneously dispersed, e.g. so that there is no significant aggregation/flocculation of the clay platelets (e.g. just prior to polymerization, e.g., at the temperature/pressure conditions of polymerization).

Said clay platelets are surface-modified as set out herein below. This ensures that the clay platelets are dispersible as platelets in the acidic aqueous liquid, i.e. comprising the polymerizable monomers or oligomers with carboxylic acid and/or carboxylate group(s). In particular when the clay platelets are small, e.g. they have a low aspect ratio, e.g. of 300 or less or for example 200 or less, or when high shear application is a problem, the aggregation in acid liquids may be a problem and the surface modification as described herein is very beneficial.

Said clay platelets and said surface-modified clay platelets in the polymerization liquid herein, e.g. prior to the polymerization reaction herein and during polymerization, and preferably in the SMC polymers, may for example have a weight average largest particle dimension (length) of less than 800 nm, preferably less than 500, preferably 300 nm or less, for example 200 nm or less, or 100 nm or less; and for example a said weight average largest particle size dimension (length) being at least 5 nm, or at least 10, or at least 20 nm.

The clay platelets and surface-modified clay platelets in said liquid, e.g. prior to the polymerization reaction herein and during polymerization, and preferably in the SMC polymers may for example have an aspect ratio of 300 or less, or 200 or less or 100 or less. The aspect ratio of clay is generally more than 5, or more than 10. (The basal surfaces are always larger than the edge surfaces.)

In the final SMC polymers the clay platelets are typically also present as individual modified platelets e.g. homogeneous, e.g. of the dimensions and aspect ratio's above, (or at least 90% or at least 95% by weight thereof), which may be determined via removal of a micro-slice of said SMC polymer gel (via a ultramicrotome) and submitting this to a cryo-TEM methods, known in the art.

The clay may be purified before surface-modification, e.g. to remove metals etc., by methods known in the art (and referred to below).

In some embodiments herein, the clay to be modified is a di-octahedral or tri-octahedral clay.

Examples of suitable clays to be modified herein are so-called swellable clays, i.e. smectite type clays, including hectorite, including laponite (i.e. synthetic clay), montmorillonite, saponite, mermiculite or kaolin, or mixtures thereof; in one embodiment, montmorillonite and/or hectorite, including laponite, are preferred. (These clays are often referred to as water swelling; however, it should be noted that, in the embodiment herein the clay are present as substantially individual clay platelets and then, they are no longer water swelling.)

Surface Modification and Modification Compounds and Resulting Surface Modified Clay The clay in the polymerization liquid has modified basal surface or "surfaces", as also referred to hereinafter. In the method herein, this may be done prior to addition of the monomers, or simultaneously with addition of the monomers. In some embodiment, the surface modification is done prior to addition of the monomers (e.g. prior to making the aqueous liquid acidic). To obtain the surface-modified clay, the clay is for example dispersed in a liquid that comprises the surface modification compound(s), and/or the clay is dispersed in a liquid, and the modification compound(s) may then be added to the dispersion, optionally also as solution or dispersion.

The ratio of clay to surface modification compound may for example be within the range of 1:1 to 100:1 (by weight, based on the weight of dry clay and dry surface modification compound).

In the following, the surface modification compounds are described as they are before addition to the clay. It should be understood that the resulting surface modified clays and the resulting SMC polymers thus comprise the corresponding reaction product of said compounds with said clay surfaces.

The surface modification compound has a moiety that, at the pH specified herein, can bind to the negatively charged basal surface of the clay platelet.

The surface-modifying compound may be a compound that has a cationic moiety (and/or: cationic at the pH of the liquid herein and reaction herein), that can bind to the negatively charged basal surface of the clay platelet. The surface modified clay may have surface(s) that are neutral (at the pH of the liquid).

For example, the surface modification compound may comprise an alkylated nitrogen moiety, or alkoxylated nitrogen moiety, including for example linear, branched or cyclic amino-, ammonium-compounds. Such moieties may be cationic at the pH of the reaction liquid/reaction.

The surface modification compound may have one or more moieties selected from amines or imines, including derivatives thereof, such as diamines or diimines and/or ethylene or poly- or oligo-ethylene derivatives thereof, including hexamethylene diamine and derivatives thereof, ethylendiamine and derivatives thereof, oligo-alkyleneimine and derivatives thereof, such as linear or branched polyethyleneimine, oligo-etheramines and derivatives thereof, linear or branched amides, or mixtures thereof.

The surface modification compound may have an acryl amide moiety. The surface modification compound may have a urethane moiety (bond by hydrogen bonding to the negative basal surface), or more preferably it may have a cationically modified urethane moiety, or further modifications thereof.

Especially preferred are moieties selected from linear or branched polyethyleneimine, hexamethylene diamine or ethylendiamine, or derivatives of any of these, or mixtures thereof.

The surface modification compound may also be a cationically modified oligo- or poly-saccharides, or derivative thereof.

In addition, the surface modification compound may have one or more further moiety that is or are hydrophilic. This can aid dispersion of the surface-modified clay in the reaction liquid and/or can further enhance the hydrophilicity, and hence affinity for hydrophilic fluids (e.g. urine, blood, saline water), of the water-absorbing SMC polymers. This may for example be anionic moiety, or —OH. In some embodiments, it is preferred that the surface modification compound has at least one moiety that is an alkoxylated moiety, carboxylated moiety, or sulfonated moiety, or sulfated moiety, to further improve hydrophilicity.

The surface modification compounds may be such that, when chemically bound to the clay surfaces, they introducing a sterically hindering moiety (s), which hinders and hence reduces aggregation of clay platelets. Hence, the surface-modification compound may have a moiety that is sterically hindering. In some preferred embodiments herein, the surface modification compound has one or more moieties that can provide sterical hindrance, having at least 6 Carbon atoms, and/or a length of at least 10 angstrom, or at least 15 angstrom. Preferred may be that this is an oligomer chain moiety.

The surface modification compound may for example have oligo-alkyleneoxide (AE) moiety, such as a oligo-ethyleneoxide (EO) moiety, for example with an average number of AO (e.g. EO)-repeating units of at least 2, preferably at least 5 or at least 10, and for example up to 100, or up to 60 or up to 40. In some embodiments herein, it may be preferred that the surface modification compound has at least a moiety that is an oligo-ethoxylate with a number of 2 to 40 repeating units.

The surface-modification compound, in particular those with a cationic group as described above, may have a further moiety or moieties that can ionically or covalently bind to the monomer or oligomer, or the polymer formed thereby; for example, the surface modification compound may have one or more unsaturated moieties (e.g. with C═C group), and/or one or more moieties that can form an ester or amide bond with the carboxyl group of the monomer, oligomer or polymer thereof, such as an oligo-ether or polyether moiety. Then, the surface modification compound not only binds with the surface of the clay platelet, but the compound(s) can also ionically or covalently bind to the polymers. In such embodiments, the clay platelets are not only surface-modified to ensure homogeneous dispersion (and hence homogeneous incorporation in the final polymers, after polymerization), but the surface modification further serves to strongly bind to the polymers, e.g. covalently/ionically. The surface modification compound described herein above, e.g. with a cationic group, may for example comprise contain a polymerizable moiety, such as an alkylene, e.g. ethylene; and/or the unsaturated moiety may for example be an ester of acrylic acid, and/or an alkylated derivatives of acrylic acid, such as methacrylic acid.

As mentioned above, it may be useful to apply during the surface modification step and/or during the preparation of the acidic polymerization liquid, (prior to commencement of the polymerization) an ultrasonic treatment step, and/or mixing step; preferred is the application of a (e.g. high) shear mixing. For example, a Y-Tron mixer can be used. The exfoliation of the clay may also be affected by use of high-shear mixers, (such as CB Loedige mixers, Schugi mixers, Littleford mixers, Drais mixers). The tip speed of any such mixers may for example be from at least 20 ms$^{-1}$, or at least 30 ms$^{-1}$ to for example 45 or 40 or 35 ms$^{-1}$.

In particular for platelets with high aspect ratios, the shear forces may be chosen such that it does not lead to fracture of the individual clay platelet. It may be beneficial to select low aspect ratio clay platelets, as defined herein after (for example of aspect ratios of 300 or less or 200 or less), for example in order to allow higher shear forces.

The surface-modification of the clay platelets may be done in any liquid. It may for example be done in water. Alternatively, the surface modification may be done in the absence of water, e.g. preferably in an anhydrous liquid, e.g. anhydrous liquid with a dielectric constant larger than 40 preferentially more than 50, for example propylene carbonate, ethylene carbonate, etc.

The clay may be mixed with the monomers and/or oligomers and simultaneously with the surface-modification compound(s). However, in some embodiments herein, it is preferred that the clay is modified prior to mixing with acidic solution of the monomers and/or oligomers herein. In some embodiments herein, it is preferred to surface modify the clay prior to addition to the liquid with monomers or oligomers. In some embodiment, it is preferred to modify the clay's surfaces, and then to wash the resulting modified clay, and/or filtrate and or/submit to dialysis the modified clay, prior to addition to the liquid with monomers or oligomers.

The clays dispersion, clay modification and/or polymerization liquid formation may for example be at temperatures around 15-25° C., or optionally under heating, for example to a temperature above 40° C., or above 45° C. or above 50° C., for example up to 90° C. or up to 70° C. or up to 60° C.). The surface-modification may alternatively or in addition be done under shear and/or temperature conditions as set out above. Furthermore, these shear and/or temperature conditions may also be applied to the polymerization liquid comprising the surface-modified clay, prior to polymerization (prior to addition of the initiator system) or optionally during part of the polymerization (until a gel is forming).

The liquid phase of the aqueous liquid comprises at least water, and it may optionally comprise other, e.g. organic, liquids, or it may consist of water. Highly preferred may be that the liquid phase comprises at least 80% by weight of water, preferably at least 90% or even 100% by weight of water.

In another embodiment of the invention, a method is provided, said method being for making an aqueous polymerization reaction liquid comprising: clay platelets with opposing basal platelet surfaces and modified platelet surfaces; and acrylic acid and/or acrylate salt monomers, the method comprising the steps of:

i.a) obtaining a first aqueous mixture, being an aqueous solution or dispersion of said acrylic acid and/or acrylate salt monomers;

i.b) obtaining a clay, optionally a clay dispersion, for example in water; and i.c) obtaining surface modification compounds, optionally a dispersion or solution thereof, for example in water;

i.d) combining i.a) and i.b) first and then this with i.c); or, combining i.a) and i.b) and i.c) simultaneously; or, combining i.b) and i.c) first and then this combination with i.a); and i.e) applying in the step(s) of i.d) a shear force mixing, e.g. a ultrasonic mixing or mechanical mixing, to obtain said aqueous polymerization reaction liquid, which has a pH of 6 or less, which comprises said polymerizable monomers, polymerizable oligomers and/or mixtures thereof, and which has homogeneously dispersed therein clay platelets with modified basal surfaces (herein referred to as "surfaces").

Then, a polymerization initiator system can be added to this liquid and, if required, the initiator can be activated, to start the polymerization of the monomers and/or oligomers (and optionally the covalently binding thereof to the surface modification compound(s), e.g. for example to a C=C moiety thereof).

The thus obtained polymerization liquid can be purged with inert gas prior to the start of the polymerization, and optionally during polymerization An organic crosslinker (i.e. not clay containing) may be added to the polymerization liquid, such as organic crosslinkers known in the art. For example, typical crosslinkers are di- or poly-functional monomers, having thus two or more groups that can be polymerized, such as N,N'-methylenebisacrylamide, trimethylolpropane triacrylate, ethylene glycol di(meth)acrylate, or triallylamine The polymerization liquid comprises for example: 0.1 to 10 wt. % surface-modified clay, 5 to 95 wt. % water; 5 to 95 wt. % monomers/oligomers, (preferably monomers), 0 to 10 wt. % organic crosslinker, optionally a dispersing aid, such as CMC, and then for example 0.01 to 5 wt. % polymerization initiator is added to that liquid, to start the polymerization.

Optional Edge Modification and Edge Modification Compounds

In some embodiment herein, the clay platelets may additionally have platelets edge(s) that are also modified, by so-called edge modification compound(s).

Said edge-modification compound is typically selected from the group consisting of:

i) phosphorylation compounds, preferably selected from the group consisting of: phosphate salts, condensed phosphate salts, derivatives thereof and acids forms thereof; phosponic acid, derivatives thereof and salts thereof; and combinations thereof;

ii) silanization compounds of the formula $SiR^{I}R^{II}R^{III}R^{IV}$, whereby the moieties $R^{I}$, $R^{II}$, $R^{III}$, $R^{IV}$ are each selected from the group consisting of the subgroups: a) Alkyl, Aryl, O-Alkyl(Alkoxy), N-Alkyls, Alkenes, alkenyls; and b) hydrogen, halide; and c) Hydroxy, Carboxy-containing moieties, Expoxy-containing moieties, Isocyano-containing moieties, provided that at least one and at the most three of said moieties are selected from the subgroup a) and that at least one and at the most three of said moieties are selected from said subgroup c) and that at the most one of said moieties is selected from said subgroup b);

iii) fluorination compounds, preferably a MF salt whereby M is a mono-valent cation.

A mixture of such edge modification compounds may be used.

The phosphorylation compound(s) may be selected from the group consisting of: phosphate salts and/or derivatives thereof and/or acids forms thereof; condensed phosphate salts, and/or derivatives thereof and/or acids forms thereof; phosponic acid, derivatives thereof and salts thereof; and combinations thereof. For example, sodium pyrophosphate decahydrate may be suitably used. Organo-phosphor derivatives may be useful herein.

The silanization compound may be an organo silane compound, e.g. of the formula: $SiR^{I}R^{II}R^{III}R^{IV}$, whereby the moieties $R^{I}$, $R^{II}$, $R^{III}$, $R^{IV}$ are each selected from the group consisting of the subgroups: a) Alkyl, Aryl, Alkoxy, N-Alkyls, Alkenes, alkenyls; and b) hydrogen, halide; and c) hydroxy, carboxy-containing moieties, expoxy-containing moieties, provided that at least one and at the most three of said moieties are selected from the subgroup a) and that at least one and at the most three of said moieties are selected from said subgroup c) and that at the most one of said moieties is selected from said subgroup b).

It may be beneficial that at least one of said moieties $R^{I}$, $R^{II}$, $R^{III}$, $R^{IV}$ is a moiety that is suitable to bond to said polymerizable monomer or polymerizable oligomer. For example, at least one of said moieties is an unsaturated moiety, such as vinyl. Useful may for example be to use as silanization compound, 7-Octenedimethylmethoxysilane.

Said edge modification compound may includes or consists of one or more fluorination compounds. This may include preferably fluoride salt, e.g. MF; in some embodiments it may be preferred that said cation M is a mono-valent counterion, such as sodium or ammonium.

In some embodiments herein, said edge modification compound may be a compound that not only modifies the charge of the edges of the clay, but also sterically hinders said platelet edges, to further reduce the risk of aggregation of the clay platelets in the acidic liquid. Thereto, said edge modification compound may have at least one moiety of at least 10 angstrom (Å) or at least 15 angstrom, or at least 20 angstrom.

Polymerizable Monomers and Oligomers

The aqueous polymerization liquid comprises polymerizable monomers (herein after referred to as monomers), and/or polymerizable oligomers of said monomer(s); (e.g. said oligomers having between 2 and typically 5000 polymerized monomers). In order to be polymerizable, the monomers, and hence the oligomers thereof, comprise a polymerizable moiety, such as a C=C moiety; preferred may be that the monomer have a single polymerizable moiety, such as a single C=C moiety.

In some preferred embodiments herein, may to use monomers in said polymerization liquid.

Furthermore, said monomers and hence said oligomers thereof, have one or more carboxylic acid and/or carboxylate moieties. Suitable monomers may for example be acrylic acid and/or acrylate monomers.

Said monomers and/or oligomers render the aqueous liquid acidic, i.e. having a pH of 6 or less, typically below 6, or even below 5.

The monomers or oligomers may be neutralized or partially neutralized in said liquid, e.g. they may comprise a carboxylate, e.g. acrylate, group with a cation counterion, e.g. the monomers (or oligomer thereof) may include or may be a carboxylate (e.g. acryalte) salt. The counter ion is typically sodium.

In some embodiments herein, at least 20% by weight (based on total of monomers or oligomers) of said monomers and/or of said oligomers are neutralized, e.g. having salt counterion. In some embodiments, this may be at least 40 mol %, or at least 50 mol % or at least 60 mol %, and it may be as high as 100 mol % or as high as 80 mol %.

The resulting SMC polymers may thus be i) SMC polycarboxylic acid polymers that are not neutralized, or ii) SMC polycarboxylate polymers, that are fully neutralized, or iii) SMC polymers that have carboylate and carboxylic acid groups, at any of the mol % levels stated above. Any of these SMC polymers i), ii) or ii) or combination thereof is herein referred to as SMC polycarboxylate and/or polycarboxlic acid polymers.

To further reduce the risk of aggregation when said neutralized monomers/oligomers are present (carboxylate salts) the edge modification compound may have a sterically hindering moiety, as described herein, and/or the clay platelets may be further modified, by having basal surface modification, as described below.

Polymerization

In order to start the polymerization in the polymerization liquid, and in order to obtain the water-absorbing SMC polymers herein, a polymerization initiator system may be added to the liquid.

This initiator system may be added in solid or liquid form, for example as a solution or dispersion in a liquid, for example an aqueous liquid, e.g. water.

This initiator system may comprise more than one type of compound to initiate the polymerization, or it may comprise a single compound.

The initiator system may need to be activated with an activator, such as an activator compound or for example heat or radiation, including light radiation, or alternatively, no activation may be needed.

The initiator system can be appropriately selected from conventional (e.g. radical) polymerization initiators (and optional catalysts). Materials which display good water dispersibility/solubility are preferred. The initiator compound(s) of the system include for example peroxides, hydroperoxides, hydrogen peroxide, persulfates, azo compounds and redox initiators. Useful organic peroxides are for example acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-tri-methylhexanoate, acetylcyclohexylsulfonyl peroxide, dilauryl peroxide, dibenzoyl peroxide and tert-amyl perneodecanoate. Preferred azo compounds include 2,2'-azobisisobutyronitrile, 2,2'-azobis(2,4-dimethylvaleronitrile) and 2,2'-azobis (4-methoxy-2,4-dimethyl-valeronitrile), especially water-soluble azo initiators, examples being 2,2'-azobis-{2-[1-(2-hydroxyethyl)-2-imidazolin-2-yl]propane}dihydrochloride, 2,2'-azobis-(2-amidinopropane)dihydrochloride, 2,2'-azobis [2-(2-imidazolin-2-yl)propane]dihydrochloride and 2,2'-azobis[2-(5-methyl-2-imidazolin-2-yl)propane]dihydrochloride. Very particular preference is given to 2,2'-azobis [2-(2-imidazolin-2-yl)propane]dihydrochloride and 2,2'-azobis[2-(5-methyl-2-imidazolin-2-yl)propane] dihydrochloride.

Useful may be for some embodiment herein: persulfates such as sodium peroxodisulfate, potassium peroxodisulfate and ammonium peroxodisulfate; hydroperoxides such as t-butyl hydroperoxide and cumene hydroperoxide; and azo compounds such as 2,2'-azobis-2-amidinopropane hydrochloride, e.g. such as VA-044, V-50 and V-501 (all manufactured by Wako Pure Chemical Industries Ltd.), and mixtures of $Fe^{2+}$; and hydrogen peroxide, or hydrogen peroxide and ascorbic acid. The latter may be preferred initiator system for use herein. In one embodiment, a mixture of two or more polymerization initiators is used, for example one of the class of azo-compounds and one of the class of peroxo or peroxide compounds, as described above. This is believed to ensure fast polymerization. As for example described in US2008/242817, the use of azo compound initiator or redox initiators is advantageous for directing the rate of polymerization.

The initiator compound or system may for example be introduced onto the polymerization reaction liquid at a level of for example at least 0.1% by weight of the polymerizable monomers or oligomers, or for example at least 0.3% or at least 0.5% or at least 0.7%, up to typically 10% or 5% or 3% by weight.

The polymerization rate can be controlled through the identity and amount of the initiator system used and the temperature used.

A polymerization catalyst may also be present, such as for example TMEDA (N,N,N',N' tetramethylethylenediamine).

The polymerization of the polymerizable monomers/oligomers may be highly exothermic, and hence, the polymerization liquid may be cooled during polymerization.

Water-absorbing SMC Polymers and Absorbent Articles Therewith

The present invention also relates to water-absorbing surface-modified clay linked polycarboxylic acid and/or polycarboxylate polymers, e.g. obtainable with the aqueous polymerization liquid described herein, or obtainable by the method using said liquid herein, herein referred to as water-absorbing SMC polymers.

"Water-absorbing polymers" or "water-absorbing SMC polymers", as used herein, refers to polymers that can absorb and retain at least 10 grams of saline (0.9% saline solution in demineralised water), per gram of polymer, as measurable by the CRC method set out herein. Obviously, the SMC polymers will absorb other aqueous liquids as well, such as urine, blood. Preferred may be that said CRC is at least 20 g/g, or at 30 g/g, or at least 40 g/g. Upper limits may for example be up to 150 g/g, or up to 100 g/g.

The water-absorbing SMC polymers herein are typically water-swellable, i.e. water-gelling, e.g. such that they swell in a 0.9% saline solution in demineralised water, by absorbing said saline water; they may thereby form a gel. Obviously, the polymers herein swell also in other liquids, like urine and blood.

Said surface-modified clay platelets form bridging point between said polymers, thereby linking said polymers. Typically, substantially all said polymers are bonded to at least one surface-modified clay platelet during said polymerization reaction, typically more than one; this may be characterized by determination of the extractable levels of the resulting SMC polymers, by the method described below. The extractable level of the SMC polymers is preferably less than 15% (by weight of said polymers), more preferably less than 10% and most preferably less than 6%, it may even be less than 3% of extractables.

In some embodiments, it is highly preferred that the polymers are also bound to said clay via the surface modification compound(s),via covalent bonding and/or ionic bonding, e.g. via a moiety of the surface modification compound(s) that can bind to the monomers, oligomers, or polymers, e.g. having a unsaturated moiety or a moiety that can react with the carboxy moiety of the monomer/oligomers/polymers.

The amount of surface modified clay present in the SMC polymers may be chosen depending on for example the required resistance against deformation and/or the required absorbency. For example from 0.1 wt % or from 0.5 wt % or from 2wt % or from 5wt %, to 40wt %,or to 30 wt %, or to 20 wt % or to 10 wt % (by weight of the polymers) of surface-modified clay may be used.

The SMC polymers may be in the form of a gel, film, or foam, or in one embodiment herein, in particulate form, which includes for the purpose of the invention particles, including flakes, fibers, agglomerates, blocks, granules, spheres.

The resulting water-absorbing SMC polymers may comprise water. Hence the resulting water-absorbing SMC polymers may be in the form of a gel. The water-absorbing SMC polymers, or gel thereof, may be further treated, e.g. dried, to obtain dry water-absorbing SMC polymers, e.g. particles thereof, for example comprising less than 10% by weight, or less than 5% by weight of liquid (e.g. water). Alternatively, or in addition, the water-absorbing SMC polymers may be further treated to obtain particulate water-absorbing SMC polymers, e.g. by conventional particle formation steps, such as wet-grinding and drying, or grinding and optionally drying, and optionally subsequent sieving to obtain eh desired particles size fraction/ranges.

The particulate water-absorbing SMC polymers may be in the form of particles with a mass median particle size up to 1 mm, or even between 10 microns and 1 mm, or preferably between 50 µm and 800 µm, as can for example be measured by the method set out in for example EP-A-0691133.

In one embodiment of the invention, at least 80% by weight of the particles have particle sizes between 10 µm and 1200 µm or even between 50 µm and 800 µm and a mass median particle size between 100 or 200, and 800 µm or 600 µm.

The water-absorbing SMC polymers or particles thereof may be further treated with surface treatments, such a surface cross-linking and/or dusting with organic and/or inorganic materials, and/or coating with inorganic and/or organic material.

The polymerization reaction may deploy also organic crosslinking compounds during the polymerization; but in some embodiments herein, the polymerization reaction is the absence of any organic crosslinking compounds. In any event, after polymerization, organic crosslinking agents may be added, e.g. for surface-crosslinking the polymer surfaces.

The water-absorbing SMC polymers, as described herein, or the particles thereof, as described herein, are useful in absorbent articles. Hence in another aspect of the present invention, absorbent articles or typically disposable absorbent articles are provided, comprising the water-absorbing SMC polymers, as described herein, or the particles thereof, as described herein.

Disposable absorbent articles herein include articles to be placed against to body of a user to absorb bodily fluids; such articles include, but are not limited to: articles to be fastened around the lower torso of a user, such as diapers (including infant (e.g. baby or toddler) diapers with fasteners, training pants, but also adult incontinence diapers and adult incontinence pants), but also articles such as adult incontinence pads, diaper liners or inserts, and also feminine hygiene articles, including sanitary napkins, panty- liners tampons, and the like.

The absorbent article herein comprises for example an absorbent structure, e.g. absorbent core, comprising the SMC polymers herein; or preferably, it may comprise additional components, such as pulp, adhesive, nonwoven material, etc. For example, the absorbent structure may also comprise one or more support or wrapping materials, such as foams, films, woven webs and/or nonwoven webs. Preferably, in particular when the absorbent structure is a storage layer of an absorbent article above, or when the absorbent structure comprises a layer that serves as storage layer, the structure or layer comprises large amounts of the SMC polymer herein, compared to possible other components of the structure; preferably the SMC polymers is present at a level of more than 50% by weight of the structure, or even more than 70% by weight, or even more than 80% by weight, or even more than 90% by weight of the structure. The absorbent structure herein may comprise a structuring agent or matrix agent, such as non-absorbent fibers, and/or a thermoplastic component, such as a thermoplastic adhesive, or for example a non-absorbing fibrous thermoplastic adhesive component. The absorbent structure may comprise, alternatively or in addition, absorbent fibrous material, such as an airfelt material cellulose fibers etc., which can provide a matrix for immobilization of the SMC polymers.

However, if the absorbent structure is a liquid storage layer or when the absorbent structure comprises one or more liquid storage layers, it may be preferred that said liquid structure or said liquid storage layer comprises large amounts of the SMC polymers herein and only very little or no absorbent (cellulose) fibers, e.g. preferably less than 40% weight of the structure, or less than 20% by weight or less than 10% by or less than 5% by weight (of said structure) of said absorbent fibrous (cellulose) material; and/or preferably more than 50% or more than 70% or more than 80% or more than 90% by weight (of the structure) of the SMC polymers herein. Preferably, the weight ratio of the SMC polymers to any optional absorbent or non-absorbent fibers, or other matrix agents, is at least 1:1, preferably at least 3:2 or at least 2:1, or at least 3:1 or at least 4:1.

Preferably the absorbent structure comprises at least a wrapping material, which wraps (the portion comprising) the SMC polymers, a so-called core wrap material. In one preferred embodiment the core wrap material comprises a top layer and a bottom layer, the latter being furthest away from the skin of the user, whereby the core wrap material as a whole or the top layer and/or the bottom layer can be provided from for example a nonwoven material, such as spunbond, meltblown and/or carded nonwovens. One preferred material is a so-called SMS material, comprising a spunbonded, a melt-blown and a further spunbonded layer.

In a preferred embodiment of the present invention the absorbent structure comprises: a wrapping material, the SMC polymers described herein, and a thermoplastic material and/or an adhesive and/or a thermoplastic adhesive, which may be in the form of non-absorbing fibers.

Preferred disposable absorbent articles herein have a topsheet and a backsheet, which each have a front region, back region and crotch region, positioned therein between. The absorbent structure with the SMC polymers of the invention is typically positioned in between the topsheet and backsheet. Preferred backsheets are vapour pervious but liquid impervious. Preferred topsheet materials are at least partially hydrophilic; preferred are also so-called apertured topsheets.

These preferred absorbent articles typically comprise a liquid impervious (but preferably air or water vapour pervious) backsheet, a fluid pervious topsheet joined to, or otherwise associated with the backsheet. Such articles are well known in the art and fully disclosed in various documents mentioned throughout the description.

Preferred diapers and training pants herein have one or more sets of leg elastics and/or barrier leg cuffs, as known in the art.

Test Methods Referred to Herein

The measurements should be carried out, unless otherwise stated, at an ambient temperature of 23±2° C. and a relative humidity of 50±10%.

Water Content

The water-content can be determined by the Edana test, number ERT 430.1-99 (February 1999) which involves drying the polymers at 105° Celsius for 3 hours and determining the moisture content by the weight loss of the polymers after drying.

Centrifuge Retention Capacity (CRC)

Centrifuge Retention Capacity as referred to herein is determined by EDANA (European Disposables and Nonwovens Association) recommended test method No. 441.2-02 "Centrifuge retention capacity".

Extractables

The extractable fractions of the water-absorbing polymeric particles are determined in accordance with EDANA (European Disposables and Nonwovens Association) recommended test method No. 470.2-02 "Extractables".

EDANA test methods are obtainable for example at European Disposables and Nonwovens Association, Avenue Eugene Plasky 157, B-1030 Brussels, Belgium.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A water-absorbing surface-modified-clay linked polycarboxylic acid and/or polycarboxylate polymer, obtainable by a polymerization reaction comprising the steps of:
    a) obtaining an aqueous polymerization reaction liquid, comprising (i) homogeneously dispersed therein, clay platelets with opposing basal platelet surfaces and platelet edges; and (ii) dissolved or homogeneously dispersed therein, polymerizable monomers comprising a carboxylic acid and/or carboxylate group, and/or polymerizable oligomers of one or more of the monomers;
        wherein the aqueous liquid has a pH of about 6 or less;
        wherein at least about 20%, by weight, of the monomers and/or oligomers are neutralized; and wherein the basal surface(s) of the clay platelets are modified with a surface modification compound(s);
    b) initiating the polymerization of the monomers and/or oligomers in the liquid of step a);
        wherein the water-absorbing surface-modified clay linked polymer exhibits a Centrifuge Retention Capacity (CRC) in a 0.9% saline solution in demineralized water, of at least about 10 g of saline per gram of polymer.

2. A method for making a water-absorbing surface-modified-clay linked polycarboxylic acid and/or polycarboxylate polymer, comprising the steps of:
    a) obtaining an aqueous polymerization reaction liquid comprising i) homogeneously dispersed therein, clay platelets with opposing basal platelet surfaces and platelet edges; and ii) dissolved or homogeneously dispersed therein, polymerizable monomers comprising a carboxylic acid group and/or carboxylate group, and/or polymerizable oligomers of one or more of the monomers;
        wherein the aqueous liquid has a pH of about 6 or less;
        wherein at least about 20%, by weight, of the monomers and/or oligomers are neutralized; and wherein the basal surface(s) of the clay platelets are modified with one or more surface modification compound(s);
    b) obtaining a polymerization initiator system;
    c) combining the liquid of a) with the polymerization initiator system of b) and polymerizing the monomers and/or oligomers;
        wherein the water-absorbing surface-modified clay linked polymer exhibits a Centrifuge Retention Capacity (CRC) in a 0.9% saline solution in demineralized water, of at least about 10 g of saline per gram of polymer.

3. A polymer as in claim 1, wherein at least about 20 mol % (based on all monomers and or oligomers) of the polymerizable monomers and/or of the polymerizable oligomers have a carboxylate group with cationic counter ion.

4. A polymer as in claim 1, wherein the reaction liquid comprises monomers that are acrylic acid and/or acrylate salt, and the polymer is a polyacrylic acid and/or polyacrylate polymer.

5. A polymer as in claim 1, wherein the one or more surface modification compound(s) has a cationic moiety capable of bonding to a clay platelet's basal plate.

6. A polymer as in claim 5, wherein the one or more surface modification compound(s) also has an anionic moiety and/or one or more hydroxyl groups.

7. A polymer as in claim 1, wherein the one or more surface modification compounds comprise a unsaturated moiety capable of covalently bonding to the polymerizable monomer or polymerizable oligomer, and/or the surface modification compound comprises a moiety capable of covalently or ionically bonding to the carboxy moiety of the monomer, oligomer or polymer.

8. A polymer as in claim 1, wherein the one or more surface modification compound(s) are one or more compounds that sterically hinder the platelet surfaces, the compound having a length of at least about 10 angstroms (Å).

9. A polymer as in claim 8, wherein the one or more surface modification compound(s) have at least one moiety comprising a carbon chain of at least 6 carbon atoms.

10. A polymer as in claim 1, wherein the one or more surface modification compounds have one or more oligoalkyleneoxide (AE) moieties.

11. A polymer as in claim 10, wherein the one or more surface modification compounds have one or more oligo-ethyleneoxide moieties.

12. A polymer as in claim 1, wherein the surface modification compound has one or more alkylated nitrogen moieties and/or alkoxylated nitrogen moieties.

13. A polymer as in claim 1, wherein the one or more surface modification compounds include or are an oligo- or poly-ethyleneimine, an oligo- or poly-ethylene diamine, or ethylene diamine, or derivative of any of these, and mixtures thereof.

14. A polymer as in claim 13, wherein the one or more surface modification compounds include or are hexamethylene diamine or ethylendiamine, or derivatives thereof, or a mixture thereof.

15. A polymer as in claim 1, wherein the polymers are additionally crosslinked by organic crosslinking compounds, or wherein the polymerization reaction liquid comprises an organic crosslinking compound.

16. A polymer as in claim 1, wherein the clay platelets have edge(s) that are modified by one or more edge-modification compound selected from the group consisting of:
   i) phosphorylation compounds;
   ii) silanization compounds of the formula $SiR^{I}R^{II}R^{III}R^{IV}$, wherein the moieties $R^{I}$, $R^{II}$, $R^{III}$, $R^{IV}$ are each selected from the group consisting of the subgroups: a) Alkyl, Aryl, O-Alkyl(Alkoxy), N-Alkyls, Alkenes, alkenyls; and b) hydrogen, halide; and c) Hydroxy, Carboxy-containing moieties, Epoxy-containing moieties, Isocyano-containing moieties, provided that at least one and at the most three of the moieties are selected from the subgroup a) and that at least one and at the most three of the moieties are selected from the subgroup c) and that at the most one of the moieties is selected from the subgroup b);
   iii) fluorination compounds; and
   iv) mixtures of any of the above.

17. A polymer as in claim 16, wherein the phosphorylation compounds are selected from the group consisting of: phosphate salts, condensed phosphate salts, derivatives thereof and acid forms thereof; phosponic acid, derivatives thereof and salts thereof, and combinations thereof.

18. A polymer as in claim 16, wherein the fluorination compounds include an MF salt wherein M is a mono-valent counterion.

19. A polymer as in claim 1, wherein the pH is from about 3 to about 5.

20. A method for making an aqueous polymerization reaction liquid suitable for making water-absorbing surface-modified-clay linked polyacrylate/poly acrylic acid polymers, the method comprising the steps of:
   a) obtaining a first aqueous mixture, being an aqueous solution or dispersion of the acrylic acid and/or acrylate salt monomers, or oligomers thereof, wherein at least about 20%, by weight, of the monomers or oligomers are neutralized;
   b) obtaining a clay or clay dispersion; and
   c) obtaining one or more surface modification compound(s) having a cationic moiety that can bind to a clay platelet's basal plate, or a dispersion or solution thereof,
   d) (i) combining the solution or dispersion of (a) and the clay or clay dispersion of (b) first, and then combining this mixture with the surface modification compound or dispersion or solution of (c); or
      (ii) combining the solution or dispersion of (a) and the clay or clay dispersion of (b) and the surface modification compound or dispersion or solution of (c) simultaneously; or
      (iii) combining the clay or clay dispersion of (b) and the surface modification compound or dispersion or solution of (c) first, and then combining this with the solution or dispersion of (a); and
   e) ultrasonic or shear force mixing at least in step d)(i), d)(ii), or d(iii);
   to obtain the aqueous polymerization reaction liquid, which has a pH of about 6 or less, which comprises the polymerizable monomers, polymerizable oligomers and/or mixtures thereof, and which has homogeneously dispersed therein clay platelets with modified basal surfaces;
   wherein the water-absorbing surface-modified clay linked polymer exhibits a Centrifuge Retention Capacity (CRC) in a 0.9% saline solution in demineralized water, of at least about 10 g of saline per gram of polymer.

21. A reaction liquid, obtainable by the method of claim 20, comprising: (i) homogeneously dispersed therein, clay platelets with opposing basal platelet surfaces and platelet edges; and (ii) dissolved or homogeneously dispersed therein, acrylic acid monomers and/or acrylate salt monomers, and/or polymerizable oligomers of one or more of the monomers; wherein the aqueous liquid has a pH of about 6 or less; and wherein the clay platelet's basal surface(s) are modified with a surface modification compound(s), having a cationic moiety capable of bonding to a clay platelet's basal plate.

22. A disposable absorbent article comprising a polymer according to claim 1.

23. A disposable absorbent article as in claim 22, wherein the absorbent article is selected from the group consisting of diapers, training pants, adult incontinence diapers, adult incontinence pants, adult incontinence pads, diaper liners, diaper inserts, sanitary napkins, panty-liners, and tampons.

24. A disposable absorbent article comprising a polymer made according to the method of claim 2.

25. A disposable absorbent article as in claim 24, wherein the absorbent article is selected from the group consisting of diapers, training pants, adult incontinence diapers, adult incontinence pants, adult incontinence pads, diaper liners, diaper inserts, sanitary napkins, panty-liners, and tampons.

* * * * *